US00PP08030P

United States Patent [19]

Laver

[11] Patent Number: Plant 8,030

[45] Date of Patent: Nov. 17, 1992

[54] MINIATURE ROSE PLANT NAME LAVGOLD

[75] Inventor: Keith Laver, Caledon East, Canada

[73] Assignee: Springwood Consultants, Ltd., Ontario, Canada

[21] Appl. No.: 674,514

[22] Filed: Mar. 22, 1991

[51] Int. Cl.[5] ..... A01H 5/00

[52] U.S. Cl. ..... Plt./8.2

[58] Field of Search ..... Plt. 8, 8.2

[56] References Cited

U.S. PATENT DOCUMENTS

P.P. 7,136 2/1990 Laver ..... Plt. 8

*Primary Examiner*—Howard J. Locker

*Attorney, Agent, or Firm*—Christie, Parker & Hale

[57] ABSTRACT

A new miniature rose plant producing yellow flowers.

1 Drawing Sheet

SUMMARY OF THE INVENTION

The present invention relates to a new distinct variety of rose plant of the miniature rose class, which was originated by my crossing as seed parent the variety known as 'Dorola' and as pollen parent the variety known as 'Julie Ann'. The varietal denomination of this new rose is 'Lavgold'.

Among the novel characteristics possessed by this new variety which primarily distinguish it from its parents and all other varieties of which I am aware are its color-fast, bright yellow flowers borne on a plant well suited for pot rose production. Lavgold propagates easily from soft wood cuttings and exhibits resistance to powder mildew. It has a dwarf habit suitable for pot rose production and good shelf life.

Asexual reproduction by propagation of cuttings of the new variety as performed in Somis, Calif. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DETAILED DESCRIPTION OF THE NEW VARIETY

The following is a detailed description of my new variety, with color terminology in accordance with the Royal Horticultural Society Color Chart (RHSCC). The terminology used in color description herein refers to plate numbers in the aforementioned color chart.

Parentage: Seedling.

*Seed parent.*—'Dorola'

*Pollen parent.*—'Julie Ann'.

Class: Miniature.

The following observations are made of specimens grown in a greenhouse environment in Somis, Calif., during the period of October to January.

FLOWER

Blooming habit: Continuous.

A. Bud:

(1) *Size.*—About 5/16-inch when the petals start to unfurl.

(2) *Form.*—Pointed ovoid.

(3) *Color.*—When sepals first divide, near 12A; When half blown, the upper sides of the petals are near 12A and the lower sides of the petals are near 12A to 12B.

(4) *Sepals.*—Color — near 138A. Surface texture — covered in fine hairs. There are normally three appendaged sepals and two unappendaged sepals with hairy edges.

(5) *Receptacle.*—Color — 138A. Shape — funnel. Size — small (about 3/16"×3/16'). Surface — smooth.

(6) *Peduncle.*—Length — short. Surface — smooth. Color — medium green. Strength — stiff, erect, slender.

B. Bloom:

(1) *Size.*—Small, average open size is about 1½ inches.

(2) *Borne.*—Singly and several together, in flat clusters.

(3) *Stems.*—Short, strong.

(4) *Form.*—When first open — high center, outer petals curl back.

(5) *Petalage.*—Number of petals under normal conditions — about 25.

(6) *Color.*—The upper side of the petals is near 12A. The reverse side of the petals is near 12A. The base of the petals is yellow. The major color on the upper side is yellow. Discoloration at the end of the first day — no change in color; at the end of the third day — no change in color.

(7) *Fragrance.*—Slight.

C. Petals:

(1) *Texture.*—Thin.

(2) *Shape.*—Deltoid.

(3) *Form.*—Tips slightly recurved, edges slightly quilled.

(4) *Arrangement.*—Imbricated (regularly arranged, shingle-like).

(5) *Petaloids in center.*—Few.

(6) *Persistence.*—Drop off cleanly.

(8) *Lasting quality.*—Long, 5-7 days.

REPRODUCTIVE ORGANS

A. Anthers:

*Size.*—Medium, many.

*Color.*—Yellow.

*Arrangement.*—Regular around styles.

B. Filaments:

*Color.*—Yellow.

C. Pollen:

*Color.*—Gold yellow.

D. Styles:

*Color.*—Red.

E. Stigmas:

*Color.*—Greenish white.

PLANT

A. Form: Bush.

B. Growth: Vigorous, dwarf, upright, branching, compact.

C. Foliage:

(1) *Size.*—Small; $2\frac{1}{4}''$ long $\times$ $1\frac{1}{4}''$ wide.

(2) *Quantity.*—Normal.

(3) *Color.*—New foliage — light green. Old foliage — dark green, semi-glossy.

D. Leaflets:

(1) *Number of leaflets on normal mid-stem leaves.*—5 or 7.

(2) *Shape.*—Pointed oval.

(3) *Texture.*—Upper side — smooth and semi glossy.

(4) *Edge.*—Serrate.

(5) *Serration.*—Single.

(6) *Petiole rachis color.*—Green.

(7) *Petiole underside.*—Smooth, with an occasional prickle.

(8) *Stipules.*—Medium, bearded and edged in glands.

(9) *Resistance to disease.*—Resistant to mildew.

E. Wood:

(1) *New wood.*—Color — light green. Bark — smooth.

(2) *Old wood.*—Color — green. Bark — smooth.

F. Prickles:

(1) *Quantity.*—On main canes from base — ordinary. On laterals from main canes — ordinary.

(2) *Form.*—Long, medium, hooked downward.

(3) *Color when young.*—Green.

G. Small prickles:

*On main stalks.*—None.

*On laterals.*—None.

I claim:

1. A new and distinct variety of rose plant of the miniature rose class, substantially as shown and described.

* * * * *

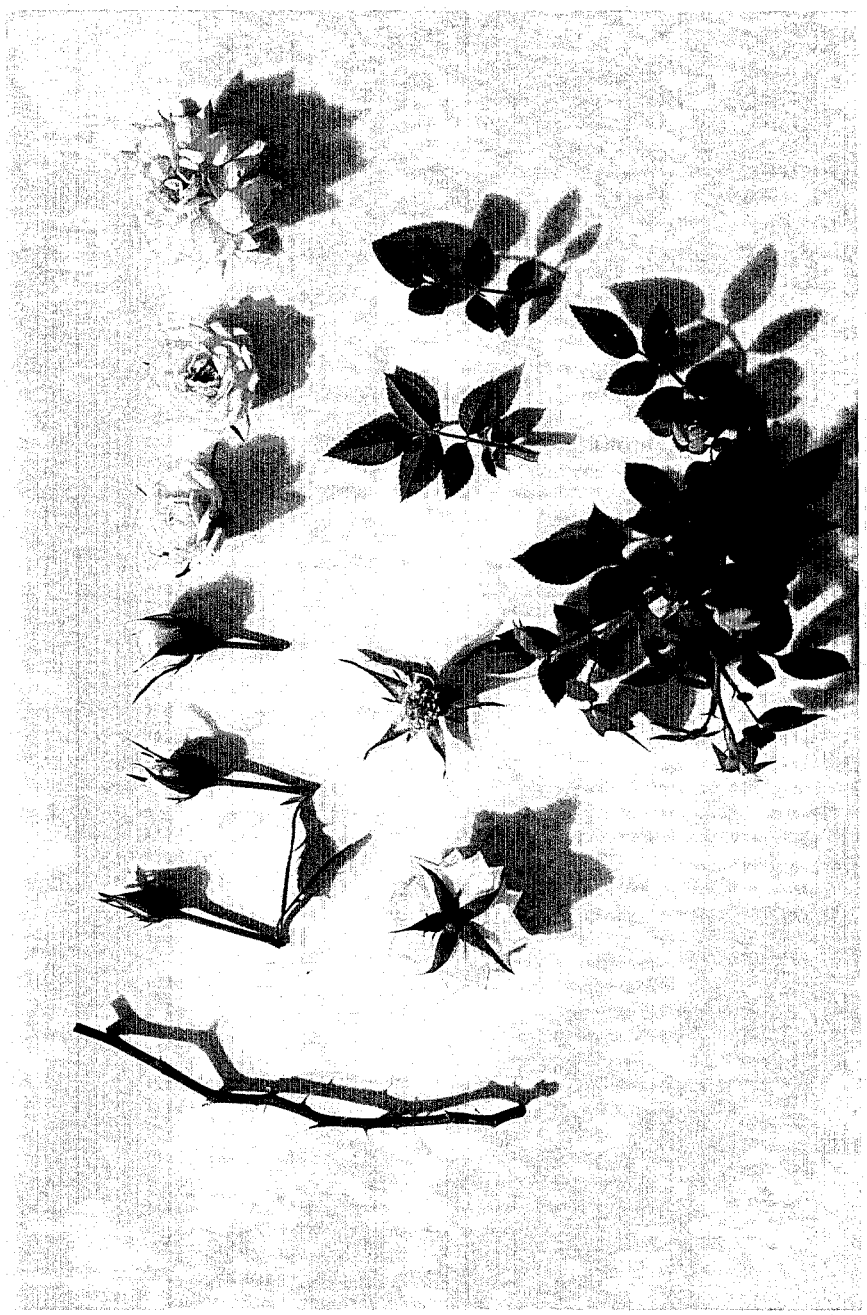

UNITED STATES PATENT AND TRADEMARK OFFICE

CERTIFICATE OF CORRECTION

PATENT NO. : Plant 8,030

DATED : November 17, 1992

INVENTOR(S) : Keith Laver

It is certified that error appears in the above-identified patent and that said Letters Patent is hereby corrected as shown below:

Column 2, line 14, change "16'" to -- 16" --.

Signed and Sealed this

Second Day of November, 1993

Bruce Lehman

*Attest:*

BRUCE LEHMAN

*Attesting Officer*

*Commissioner of Patents and Trademarks*